United States Patent [19]

Whitesides et al.

[11] Patent Number: 5,460,806
[45] Date of Patent: Oct. 24, 1995

[54] BIS(2-MERCAPTOETHYL) SULFONE

[75] Inventors: George M. Whitesides, Newton, Mass.; Guy V. Lamoureux, Burnaby, Canada

[73] Assignee: President and Fellows of Harvard College, Cambridge, Mass.

[21] Appl. No.: 80,331

[22] Filed: Jun. 22, 1993

[51] Int. Cl.$^6$ .................................................. A61K 7/09
[52] U.S. Cl. ........................................ 424/70.5; 424/70.2
[58] Field of Search ........................ 424/71, 70.2, 70.5; 568/28, 29

[56] References Cited

U.S. PATENT DOCUMENTS

| | | | |
|---|---|---|---|
| 2,505,366 | 4/1950 | Schoene | 528/375 |
| 2,870,215 | 1/1959 | Davis, Jr. et al. | 568/34 |
| 3,479,408 | 11/1969 | Perrino et al. | 568/29 |
| 3,884,951 | 5/1975 | Oswald | 560/357 |
| 5,378,813 | 1/1995 | Whitesides et al. | 530/404 |

OTHER PUBLICATIONS

Gilbert, 63 *Adv. Enzymol.* 69, 1990.
Glazer and Smith, *The Enzymes*, vol. III, 3rd ed. (Ed. P. D. Boyer) Academic: New York, 1971 pp. 501–546.
Weiss et al., 109 *J. Am. Chem. Soc.* 7201, 1987.
Thompson et al., 28 *Biochemistry* 5735, 1989.
Masamune et al., 61 *Pure Appl. Chem.* 303, 1989.
Holmgren, 54 *Annu. Rev. Biochem.* 237, 1985.
Golik et al., 109 *J. Am. Chem. Soc.* 3461, 1987.
Golik et al., 109 *J. Am. Chem. Soc.* 3462, 1987.
Lee et al., 109 *J. Am. Chem. Soc.* 3464, 1987.
Lee et al., 109 *J. Am. Chem. Soc.* 3466, 1987.
Singh and Whitesides, 56 *J. Org. Chem.* 2332, 1991.
Lees et al., 56 *J. Org. Chem.* 7328, 1991.
Jocelyn, 143 *Methods Enzymol.* 246 1987.
Cleland, 3 *Biochemistry* 480, 1964.
Whitesides et al., 42 *J. Org. Chem.* 332, 1977.
Lamoureaux and Whitesides, 58 *J. Org. Chem.* 633, 1993.

*Primary Examiner*—Robert E. Sellers
*Assistant Examiner*—Robert H. Harrison
*Attorney, Agent, or Firm*—Lyon & Lyon

[57] ABSTRACT

Bis(2-mercaptoethyl) sulfone and methods of its use as a reducing reagent.

7 Claims, No Drawings

BIS(2-MERCAPTOETHYL) SULFONE

This invention was made with government support from NIH grant GM30367 and ONR grant N00014-86-K-0756. The government has certain rights in the invention.

BACKGROUND OF THE INVENTION

This invention relates to synthesis of dithiols as reducing agents for disulfides.

The oxidation state of sulfhydryl groups influences the structure and activity of many biological systems; the thiol/disulfide interchange reaction is important in determining this state (Jocelyn, *Biochemistry of the SH Group*, Academic: London, 1972; and Gilbert, 63 *Adv. Enzymol.* 69, 1990). For example, thiol/disulfide interchange is important in the folding of proteins. Many enzymes require a cysteine in their active sites for catalysis: the thiol proteases (Glazer and Smith, *The Enzymes Vol. III*, 3rd ed., (Ed. P. D. Boyer) Academic: New York, 1971, pp. 501–546), enolase (Weiss et al., 109 *J. Am. Chem. Soc.* 7201, 1987), β-ketoacylthiolase (Thompson et al., 28 *Biochemistry* 5735, 1989; and Mesamune et al., 61 *Pure Appl. Chem.* 303, 1989), and thioredoxin (Holmgren, 54 *Annu. Rev. Biochem.* 237, 1985) are rendered inactive by oxidative conversion of the reactive thiol group to a disulfide. Thiol/trisulfide interchange has been implicated as the "triggering event" in the cleavage of DNA by calichemicin and esperamicin. (Golik et al., 109 *J. Am. Chem. Soc.* 3461, 1987; Golik et al., 109 *J. Am. Chem. Soc.* 3462, 1987; Lee et al., 109 *J. Am. Chem. Soc.* 3464, 1987; and, Lee et al., 109 *J. Am. Chem. Soc.* 3466, 1987.)

In an effort to develop reagents useful in controlling thiol/disulfide interchange in aqueous solutions, we have previously examined a number of dithiols for their usefulness as reducing agents for disulfides. (Singh and Whitesides, 56 *J. Org. Chem.* 2332, 1991; and Lees et al., 56 *J. Org. Chem.* 7328, 1991.) Although several other reagents are already available for this reaction (Jocelyn, 143 *Methods Enzymol.* 246, 1987), there is still room for improvement. Dithiothreitol (DTT, Cleland's reagent) is one reagent that is widely used for reduction of a disulfide bond. (Cleland, 3 *Biochemistry* 480, 1964). It is a strong reductant, but expensive. It is also kinetically slow at pH=7. Mercaptoethanol (ME) is inexpensive, but it is a weak and slow reducing agent, and formation of mixed disulfides with ME is common.

We wished to design a reagent that would have properties superior to the compounds presently in use for the reduction of disulfide bonds. The practical properties that are important in the design of dithiols for the efficient reduction of acyclic disulfides are high solubility in aqueous solutions, low cost, low odor, and low toxicity. (Whitesides et al., 42 *J. Org. Chem.* 332, 1977). We were especially interested in the rate of reduction and the redox potential. In actual practice, rates of reduction that are 5–7 times faster than DTT have been observed (Lees et al., supra).

In addition to a fast rate of reduction, a useful dithiol should be strongly reducing in order to reduce disulfides quantitatively and to maintain thiols in the reduced state without the inconvenience of mixed disulfides. Since DTT is one of the most strongly reducing dithiols, the larger the equilibrium constant for thiol/disulfide exchange between a dithiol and $DTT_{ox}$, the stronger the reductant. We have used this equilibrium to evaluate several dithiols in terms of their reduction strength.

SUMMARY OF THE INVENTION

The present invention relates to a reagent that has properties superior to compounds presently used for reduction of disulfide bonds. The compound bis(2-mercaptoethyl) sulfone was synthesized in two steps from divinyl sulfone. This compound is advantageous over existing reducing reagents such as dithiothreitol (DTT) since it has a $pK_a$ of about 7.9 and an equilibrium constant of about 63 relative to oxidized mercaptoethanol. In addition, aqueous solution of the dithiol shows no signs of decomposition over several days when protected from atmospheric oxygen.

Thus, the invention features bis(2-mercaptoethyl) sulfone and methods for its use as a reducing agent (or as an oxidation-preventing agent) in various biochemical and related procedures.

Other features and advantages of the invention will be apparent from the following description of the preferred embodiments thereof, and from the claims.

DESCRIPTION OF THE PREFERRED EMBODIMENTS

The following is taken from Lamoureux and Whitesides, 58 *J. Org. Chem.* 633, 1993, hereby incorporated by reference herein. The general methodology and equations used for analysis are presented there, and are not repeated here.

Bis(2-mercaptoethyl) sulfone (2) was synthesized in two steps from divinyl sulfone.

Divinyl sulfone (1.0 mL, 10 mmol) was added dropwise to a solution of thiolacetic acid (1.4 mL, 20 mmol) and triethylamine ($Et_3N$) (2.8 mL, 20 mmol) in anhydrous dimethylformamide (DMF) (10 mL) cooled to 0° C. The resulting orange solution was slowly warmed to room temperature (about 20°–25° C.) and was stirred for 36 hours under Argon. The solvent was removed in vacuo, and the brown residue was filtered through a plug of silica gel (50% ethyl acetate/hexane as eluant). A light-brown solid was isolated. This material was recrystallized from $CCl_4$ to provide white crystals of the bis(thiolacetate) product (2.35 g, 87%), which was pure by spectroscopic (NMR) analysis: mp 82°–83° C.; IR (thin film) 2997, 1679, 1422, 1284, 1268, 1230, 1151, 1109, 929, 514 $cm^{-1}$; $^1H$ NMR ($CDCl_3$, 400 MHz)δ3.27 (m, 8H, $SCH_2CH_2SO_2$), 2.37 (s, 6H, $COCH_3$) ppm; $^{13}C$ NMR ($CDCl_3$, 100 MHz)δ194.8, 52.7, 30.5, 21.8 ppm; TLC $R_f$=0.25 (50% ethyl acetate/hexane); MS (Pos. CI with $NH_3$) calculated for $C_8H_{14}O_4S_3$ m/e 270, found m/e 288 (M+ 18). Analysis calculated for $C_8H_{14}O_4S_3$: C, 35.54; H, 5.22; found: C, 35.36; H, 5.13.

The bis(thiolacetate) (0.612 g, 2.26 mmol) was dissolved in 1.2M HCl/MeOH (50 mL), and the clear solution was left at 23° C. for 48 hours. The solvent was removed in vacuo to yield a light-yellow solid (0.42 g, 100%) which was pure by spectroscopic (NMR) analysis. An analytical sample was prepared by recrystallization from hexane to provide pure product (0.38 g, 90%) as white, fluffy crystals: mp 57°–58° C.; IR (thin film) 2295, 2567, 1306, 1248, 1124, 729, 502 $cm^{-1}$; $^1H$ NMR ($CDCl_3$, 400 MHz)δ3.33 (m, 4H, $SCH_2CH_2SO_2$), 3.00 (m, 4H, $SCH_2CH_2SO_2$), 1.80 (t, J=8.5 Hz, 2H, SH) ppm; $^{13}C$ NMR ($CDCl_3$, 100 MHz)δ57.2, 16.8 ppm; MS (Pos. CI with $NH_3$) calculated for $C_4H_{10}O_2S_3$ m/e 186, found m/e 204 (M+18). Analysis calculated for $C_4H_{10}O_2S_3$: C, 25.79; H, 5.41; found: C, 25.67; H, 5.32.

This dithiol has also been made on a larger scale without chromatography. A solution of divinyl sulfone (17 mL, 0.15 mol) in anhydrous DMF (100 mL) was added dropwise to a solution of thiolacetic acid (22 mL, 0.30 mol) and Et$_3$N (42 mL, 0.30 mol) in anhydrous DMF (500 mL) cooled to 0° C. The resulting orange solution was slowly warmed to room temperature and was stirred for 16 hours under argon. The solvent was removed in vacuo (high vacuum) to yield 47 g of a brown solid. This residue is taken to the next step without purification. The bis(thiolacetate) was dissolved in 1.2M HCl/MeOH (500 mL), and the orange solution was left at 30° C. for 18 hours. The solvent was removed in vacuo to leave a brown solid. This residue was recrystallized from deoxygenated, distilled H$_2$O (with the addition of decolorizing charcoal to remove impurities) to provide the dithiol 2 (20 g, 72%) as white crystals (mp 57°–58° C.) with identical properties as the previous material.

Uses

Bis(2-mercaptoethyl) sulfone is useful in many reactions in place of the above-described reducing agents, especially DTT. Those of ordinary skill in the art will recognize that bis(2-mercaptoethyl) sulfone may simply be substituted for DTT but may be used in lower amounts, or for shorter time periods in standard reducing reactions. This sulfone is also useful as a hair straightening compound, such as described by DenBeste, U.S. Pat. No. 4,898,726 for another disulfide reducing agent, and as a hair curling compound in appropriate formulations well known to those in the art. Such an agent is useful in treating human hair and animal wool or fur. Specifically, the sulfone is useful in a method of maintaining a chemical comprising a thiol group and preventing the chemical from being oxidized to a disulfide by maintaining an oxidation-preventing concentration of Bis (2-mercaptoethyl) sulfone in contact with the chemical. Preferably, the chemical is a protein, or is present in hair, and the method includes shaping hair to a desired appearance and includes the step of exposing hair to the sulfone at a pH suitable for shaping the hair, allowing the exposed hair to set, and rinsing the hair to remove the sulfone. In other preferred embodiments, the hair is selected from the group consisting of human hair, animal fur, and animal wool.

Other embodiments are within the following claims.

We claim:

1. Method for reduction of an acyclic disulfide bond in a chemical, comprising the steps of contacting said chemical with an effective reducing amount of bis(2-mercaptoethyl) sulfone.

2. Method of maintaining a chemical comprising a thiol group, and preventing said chemical from being oxidized to a disulfide, by maintaining an oxidation-preventing concentration of bis(2-mercaptoethyl) sulfone in contact with said chemical.

3. The method of claim 1 or 2, wherein said chemical is a protein.

4. The method of claim 1 or 2, wherein said chemical is present in hair.

5. The method of claim 4, wherein said hair is selected from the group consisting of human hair, animal fur and animal wool.

6. Method for reduction of an acyclic disulfide bond in a chemical, comprising the steps of contacting said chemical with an effective reducing amount of bis(2-mercaptoethyl) sulfone, wherein said method comprises shaping hair to a desired appearance and includes the steps of exposing hair to said sulfone at a pH suitable for shaping the hair, allowing the exposed hair to set, and rinsing the hair to remove the sulfone.

7. Method of maintaining a chemical comprising a thiol group, and preventing said chemical from being oxidized to a disulfide, by maintaining an oxidation-preventing concentration of bis(2-mercaptoethyl sulfone in contact with said chemical, wherein said method comprises shaping hair to a desired appearance and includes the steps of exposing hair to said sulfone at a pH suitable for shaping the hair, allowing the exposed hair to set, and rinsing the hair to remove the sulfone.

* * * * *